US006545167B1

(12) United States Patent
Moorty et al.

(10) Patent No.: US 6,545,167 B1
(45) Date of Patent: Apr. 8, 2003

(54) SIMPLE AND EFFECTIVE MANUFACTURING PROCESS FOR LARGE SCALE RECOVERY OF NIMBIN, A NEEM SEED CONSTITUENT

(75) Inventors: S. R. Moorty, Karol Bagh (IN); A. Dilip Kumar, Kavadiguda (IN)

(73) Assignee: Fortune Bio-Tech Limited, Annam Garden (IN)

( * ) Notice: Subject to any disclaimer, the term of this patent is extended or adjusted under 35 U.S.C. 154(b) by 0 days.

(21) Appl. No.: 10/163,502

(22) Filed: Jun. 7, 2002

Related U.S. Application Data

(63) Continuation of application No. 10/115,073, filed on Apr. 4, 2002.

(51) Int. Cl.[7] ............................................ C07D 307/77
(52) U.S. Cl. ...................................................... 549/457
(58) Field of Search .......................................... 549/457

(56) References Cited

U.S. PATENT DOCUMENTS

| | | | |
|---|---|---|---|
| 4,943,434 | A | 7/1990 | Lidert et al. |
| 5,298,247 | A | 3/1994 | Godrej et al. |
| 5,370,873 | A | 12/1994 | Udeniya |
| 5,395,951 | A | 3/1995 | Nagasampagi et al. |
| 5,501,855 | A | 3/1996 | Talwar et al. |
| 5,602,261 | A | 2/1997 | Nagasampagi et al. |
| 5,663,374 | A | 9/1997 | Nagasampagi et al. |
| 5,698,423 | A | 12/1997 | Holowach-Keller et al. |
| 5,730,986 | A | 3/1998 | Bandyopadhyay et al. |
| 5,837,763 | A | 11/1998 | Ferraro et al. |
| 5,856,526 | A | 1/1999 | Sankaram et al. |
| 5,885,600 | A | 3/1999 | Blum et al. |
| 5,900,453 | A | 5/1999 | Egami et al. |
| 6,060,075 | A | 5/2000 | Rao et al. |

OTHER PUBLICATIONS

Nagasampagi B.A., "Development of Neem Chemistry in Inida" pp. 59–68, 1964.
Siddiqui et al., "Utilization of Nim Oil and its Bitter constituents (Nimbidin series) in the pharmaceutical Industry", J. Sci. Indust. Res. (1945), 45:5–10.
Narayanan et al., "The Molecular Formula of Nimbin", Chem. Industr. (1962), pp. 1283.
Narayanan et al., "Stereochemistry of Nimbin", Chem. Indust. (1964), p. 324.
Narayanana et al., "Structure of Nimbin", Chem. Indust. (1964), pp 322–323.

*Primary Examiner*—Deborah C. Lambkin
(74) *Attorney, Agent, or Firm*—Roylance, Abrams, Berdo

(57) ABSTRACT

Methods are disclosed for the large-scale isolation of 98.5% pure Nimbin from Neem seeds. The ultimate product is obtained first from an alcoholic extraction with subsequent partitioning using chlorinated hydrocarbon solvents. A resulting partitioned layer, which is recovered and concentrated, is then stripped with a hydrocarbon solvent, distilled and cooled to ambient temperature. The resulting mass is mixed and washed in a second hydrocarbon solvent, after which the resulting solid is washed in methanol and treated with activated carbon to produce a crystalline, tasteless product having a melting point of approximately 210–212° C.

22 Claims, No Drawings

SIMPLE AND EFFECTIVE MANUFACTURING PROCESS FOR LARGE SCALE RECOVERY OF NIMBIN, A NEEM SEED CONSTITUENT

This Appln is a Con of Ser. No. 10/115,073 Apr. 4, 2002.

OBJECT OF THE INVENTION

The present invention relates to an economically beneficial, hence, inexpensive, method which is simple avoiding labor intensive techniques, such as HPLC or column chromatography, for large-scale isolation of Nimbin. Specifically, the invention relates to a method of using a combination of alcohol solubilization, organic partitioning and crystallization to obtain highly purified Nimbin from Neem kernels.

BACKGROUND OF THE INVENTION

Nim, Neem or Nimba (*Melia azadiracta, Melia indica*) is native to India and is cultivated to a large extent because of its medicinal properties. These therapeutic properties are so highly valued to the indigenous population that the nim tree plays the role of "village dispensary" in many rural areas (Siddiqui and Mitra, *J Sci Indus Res* (India) 4:5 (1945)). Its twigs are used as a toothbrush for general oral hygiene and the leaves and bark are employed for a variety of uses including wound healing and treatment of various skin ailments (Siddiqui and Mitra, (1945)).

The first report of the pesticidal properties of Neem appeared around 1927 when Mann and Burns (*Agr J India* (Calcutta) 22:325 (1927)) observed during the locust cycle of 1926–27 that adult locusts did not feed on Neem leaves. This was followed by Chopra (*Rept of Dept of Agr* (Punjab) Pt. 2, 1:67 (1928)) who treated the extact of Neem leaves as contact poison on grub weevils.

Since then, a number of publications describing the various activities from different parts of the Neem tree have appeared. For example, Neem oil has shown antifeedant activity against *Nephotettix virescens* (leafhopper of rice). (*Neem Newsletter* 1:28 (1984)).

Azadirachta Idica (Neem) seed kernels contain the active constituents which have interested a number of workers since Chaterjee and Sen (*Ind J Med Res* (1920) 8:356) reported the isolation of margosic acid in 1919. The investigation of the bitter principles continued often with conflicting results. (See, e.g., Siddiqui, *Curr Sci* (India) 11:278 (1942)). In 1923, Wetson et al. (*J Soc Chem Ind* (1923) 42:387) isolated from the soap lye of the oil, a sulfur-free crystalline acid margoso-picrin (yield 0.12 to 0.017% oil and 0.15 to 0.24% amorphous bitter acids). Sen and Bennerjee (*J Ind Chem SOC* (1931) 8:773) noted the isolation of a sulfur-containing acidic bitter principle from aqueous extracts of the oil. Quadrat-I-Khuda et al. (*J Ind Chem SOC* (1940) 17:189) reported the isolation of a sulfur-containing essential oil and an amorphous, water-soluble bitter principle from an aqueous extract of the oil previously distilled to remove steam-volatile products. Industrial methods for isolation of such bitter principles have been reported to give yields of approximately 1.2%.

Neem seeds contain close to 100 molecules of which 84 have been identified. Nimbin was first isolated by Siddiqui in 1942 but its structural elucidation was accomplished by Narayanan et al. (*Chem & Ind* (1962) 1238; *Chem & Ind* (1964) 322; *Chem & Ind* (1964) 324; *J Chem* (1964) 2:108) and Harris et al. (*Tetrahedron* (1968) 24:1517) in the sixties. Merck Index ($12^{th}$ ed.) (1996) describes Nimbin as the first bitter principle from various parts of nim tree, *Azadirachta indica,* Juss., having a melting point of 205° C.

On account of the medicinal and antifeedant uses of nim, increased efforts have been made by different investigators to isolate the active ingredients which account for the above properties. In view of the growing importance of Neem kernel and its constituents as commercial products, the present inventors teach a method of isolating one of the active principles in a more efficient and practical manner which comports with industrial production.

SUMMARY OF THE INVENTION

The object of the present invention is to provide a simplified method for large-scale extraction of pure Nimbin from Neem kernel powder comprising extracting Neem kernel powder with alcoholic solvents. In a related aspect, the solvents can include methanol, ethanol and isopropanol.

The invention also envisages concentrating the alcoholic extract under vacuum, to include separating sugars and starches by partitioning between water and chlorinated hydrocarbon layers. Such chlorinated hydrocarbons include but are not limited to dichioromethane, dichioroethane and trichloroethylene. The method also comprises filtering the chlorinated hydrocarbon extract, stripping and precipitating the extract with a hydrocarbon solvent (e.g., hexane, heptane, octane). Moreover, the hydrocarbon extract is stripped, suspended and stirred in twice the volume of hydrocarbon. The mixture then can be cleared (e.g., by centrifugation), and the resulting solids suspended in 3 times the volume of alcohol where the material is stirred, centrifuged, dried and re-crystallized twice with alcohol and activated carbon.

Another object of the present invention is to provide a process for the preparation of essentially 98.50% pure Nimbin from pulverized Neem kernels. In a related aspect, the Nimbin obtained by the present method has a melting point of 210–212° C. and is tasteless.

The resulting compound may be formulated into many different compositions, such as lotions, sprays, cremes and the like for use on humans, animals and vegetation.

Other features and objects of the present invention will become apparent from the following description.

DETAILED DESCRIPTION OF THE INVENTION

The method employed for the isolation of the bitter products does not involve the initial saponification of the oil and is based on the difference in the solubilities of the various constituents in diluted alcohol and other non-miscible organic solvents such as ether, petroleum ether and ethyl acetate. Apart from the fact that such a method ensures the isolation of the constituents in a native form, the method has the advantage of yielding a comparatively purified oil which can be used for industrial purposes (e.g., photodegradation products of Nimbin have insecticidal activity).

According to the invention, Neem kernels are pulverized and extracted with alcoholic solvents including, but not limited to, methanol, ethanol or isopropanol. Methanol is a preferred alcohol. Alcohol is added at approximately 1–5 times the volume by weight of kernel powder at about 25–50° C. for between about 2 hours to about 24 hours under agitation. In a preferred embodiment, the ratio of alcohol to kernel powder is 2, 3 or 4, preferably 2.5. In a related aspect, the incubation temperature is about 30° C., 40° C., 45° C. or 47° C. In a preferred embodiment, the temperature is 40° C.

The incubation can occur for 3, 5, 7, 9, 11, 13, 15 or more hours. In a related aspect, longer incubation times are not necessary and 2, 4, 6 or 8 hours of incubation can be sufficient. A preferred incubation range is 4 to 6 hours. In one embodiment, when the incubation temperature is 40° C., the temperature is reduced to 30° C. before separation of the phases. In a related aspect, the temperature is brought down to about 25° C. and treated to separate the liquid and solid phases.

The solid phase can be re-extracted with an excess of about 1.5–4 times the volume of alcohol by original weight of kernel powder under the similar conditions. A preferred alcohol is methanol. It is preferred that the same alcohol is used for both extractions. A preferred ratio of alcohol to kernel powder is 1.5. The solid phase is stripped of solvent and stored.

Both liquid phases are pooled and solvent concentrated to approximately 5% of the original volume. A suitable means of concentration is evaporation, the liquid being passed successively through falling film and wiped film evaporators under reduced pressure (600 mm Hg). The resultant gummy mass containing Neem limonoids in addition to sugars, starches and lipids is partitioned between water and a chlorinated hydrocarbon solvent. Suitable chlorinated hydrocarbon solvents include but are not limited to, methylene dichloride, ethylene dichloride and trichloroethylene. In a preferred embodiment, ethylene dichloride and water are used to extract active principles from Neem kernels. In a related embodiment, aqueous and organic phases are separated, the organic phase is filtered and stripped of solvent under reduced pressure (about 600 mm Hg).

While the thick organic mass is being stirred, 2–10, preferably 4–10 and more preferably, 6–8 times the volume of hydrocarbon solvent (to include but not limited to aliphatic solvents such as hexane, heptane and octane) are added. In a preferred embodiment, hexane is added and stirred. The mixture is transferred to remove the hydrocarbon solvent, for example, under vacuum to a distillation still. The residue, a syrupy mass, contains a mixture of Neem limonoids and lipids from which Nimbin is isolated The syrupy mass is added to a hydrocarbon solvent (e.g., including, but not limited to, hexane, heptane and octane). In a preferred embodiment, heptane is the solvent. In a related aspect, the hydrocarbon is added at 2–5 times the volume, preferably 2.5 times the volume. A thick mass separates out which is collected by centrifugation. The solid mass then is cleared (e.g., spun) for 15 minutes in the centrifuge and washed with the hydrocarbon solvent. Spinning is continued and the product is unloaded from the centrifuge. In a preferred embodiment, the spring is carried out by centrifugation in an appropriate centrifugation device designed for industrial use/capacity. In a related embodiment, centrifugation speed is between about 1000 and 1600 rpm. The solid phase then is suspended in 3 times w/v of an alcoholic solvent, including, but not limited to, methanol, ethanol and isopropanol. In a preferred embodiment methanol is added, the mixture is stirred for 30 minutes and centrifuged. The product is washed in the centrifuge with the same solvent and dried under vacuum.

The result is technical grade Nimbin of 90%+purity with a melting point of 185–190° C. The product is crystallized twice with methanol 1:20 w/v. After the second re-crystallization, Nimbin of essentially 98.5% purity is obtained, which is white, crystalline, tasteless and melts between about 210° and about 212° C.

The Nimbin of the instant invention has broad spectrum insecticidal action against several classes of insects including but not limited to Lepidoptera such as diamondback moth, imported cabbage worm, cabbage looper, tobacco budworm; Coleoptera such as Colorado potato beetle; Homoplera such as green apple aphid, green peach aphid; and Homoptera such as potato leafhopper.

For the control of insects in agriculture and horticulture the dosage of the composition is calculated based on the concentration of Nimbin in the extract In general, a dosage corresponding to from about 0.1 gram to about 10 kilograms of Nimbin per hectare may be used and from about 5 grams to about 200 grams per hectare of Nimbin is preferred. The exact amount of dosage for a given situation can be routinely determined and depends on a variety of factors, for example, the substance used, the kind of pest, the formulation used, the state of the crop infested with the pest and the prevailing weather conditions. The term "insecticidal" as employed in the specification and claims of the application is to be construed as any means which adversely affects the existence or growth of the target insects. Such means can comprise a complete killing action, eradication, arresting in growth, inhibition, reducing in number or any combination thereof. The term "control" as employed in the specification and claims of this application is to be construed as meaning "insecticidal" or protecting plants from insect damage. By "insecticidally effective amount" is meant that dosage of active substance sufficient to exert insect "control."

The Nimbin of the present invention, for practical applications, can be utilized in the form of compositions or formulations. Examples of the preparation of compositions and formulations can be found in the American Chemical Society publication "Pesticidal Formulation Research," (1969), Advances in Chemistry Series No. 86, written by Wade Van Valkenburg. In these compositions and formulations, the active substance is mixed with conventional inert agronomically acceptable (i.e., plant compatible and/or pesticidally inert) diluents or extenders such as solid type usable in conventional compositions or formulations as is well known in the art. If desired, adjuvants such as surfactants, stabilizers, antifoam agents and antidrift agents may also be added.

Examples of compositions and formulations according to the invention are those known to one skilled in the art and include aqueous solutions and dispersions, oily solutions and oil dispersions, pastes, dusting powders, wettable powders, emulsifiable concentrates, flowables, granules, baits, invert emulsions, aerosol compositions and fumigating candles.

The compositions and formulations are prepared in a known manner to one skilled in the art, for example by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents.

Adhesives such as caxboxymethylcellulose and natural and synthetic polymers in the form of powders, granules or lattices, such as gum arabic, polyvinyl alcohol, polyvinyl cellulose, and polyvinyl acetate, can be used in the formulations to improve the adherence of this pesticide. Furthermore, a lubricant such as calcium stearate or magnesium stearate may be added to a wettable powder or to a mixture to be granulated.

The Nimbin of the present invention may be employed alone and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists, etc., if desired, or in the form of particular dosage preparations for specific applications made therefrom, such as solutions, emulsions, suspensions, powders, pastes, and granules which are thus ready for use.

As concerns commercially marketed preparations, these generally contemplate carrier composition mixtures in which the Nimbin is present in an amount substantially between about 0.1% and 99% by weight, and preferably between about 1% and 75% by weight, of the mixture. Carrier composition mixtures suitable for direct application in the field generally contemplate those in which the Nimbin present in the extract is used in an amount substantially between about 0.0001% and 5%, preferably between about 0.001% and 3%, by weight of the mixture. Thus the instant invention contemplates overall formulations and compositions which comprise mixtures of a conventional dispersible carrier such as (1) a dispersible inert finely divided carrier solid, and/or (2) a dispersible carrier liquid such as an inert organic solvent and/or water, with or without a surface-active effective amount of a carrier vehicle assistant (e.g., a surface-active agent, such as an emulsifying agent and/or a dispersing agent), and an amount of the Nimbin generally between about 0.0001% and about 99% by weight of the composition, preferably between about 0.001% and about 90% by weight of the composition, and more preferably between about 0.01% and about 75% by weight of the composition which is effective to control insects.

The hydrogenated extracts can be applied as sprays by methods commonly employed, such as conventional high-gallonage hydraulic sprays, low gallonage sprays, ultra low volume sprays, airblast spray, aerial sprays, and dusts.

Furthermore, the present invention contemplates methods of selectively killing, combating or controlling pests, which comprises contacting insects with a correspondingly combative or toxic amount (i.e., an insecticidally effective amount) of the Nimbin of the invention alone or together with a carrier vehicle (composition or formulation) as noted above.

The term “contacting” as employed in the specification and claims of this application is to be construed as applying to at least one of (a) such insects and (b) the corresponding habitat thereof (i.e., the locus to be protected, for example, to a growing crop or an area where a crop is to be grown) the active compound of this invention alone or as a constituent of a composition or formulation.

It will be realized, of course, that the concentration of the particular Nimbin utilized in admixture with the carrier vehicle will depend upon such factors as the type of equipment employed, method of application, area to be treated, types of pests to be controlled and degree of infestation. In addition to the aforementioned ingredients, the preparations according to the invention may also contain other substances commonly used in preparations of this kind.

The compounds of this invention can be administered to hosts for therapeutic applications by oral, parenteral (intramuscular, intraperitoneal, intravenous (IV) or subcutaneous injection), nasal, vaginal, rectal, or sublingual routes of administration, and can be formulated in dosage forms appropriate for each route of administration. A preferred route is topical.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs. These liquid dosage forms may contain inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

Topical preparations can take the form of ointments, salves and creams, for example. Known diluents, suspending agents, amphipathic agents and so on, are known in the art.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment desired. Generally dosage levels of between 0.001 to 10 mg/kg of body weight daily are administered to mammals.

For example, pure Nimbin has been consumed orally (10 mg/day) in a test study to observe therapeutic/pharmacological effects of the compound various systems/maladies in humans. In a related aspect, Nimbin has been found to have analgesic effects and topical administration modulates the tone of the skin. Further, systemic administration seems to have regressive actions on benign tumors.

The following illustrates the efficacy and advantages associated with the instant manufacturing process in accordance with the present invention. It is understood that such is for illustration purposes only and that alternative embodiments are contemplated as within the scope of the present invention.

EXAMPLE

Three thousand kg of Neem kernel are powdered by passing Neem seeds through a pulverizer and the powder is transferred through a chain conveyor into a 15000 L stainless steel extractor containing methanol (7500 L) under agitation, provided with a jacket for heating and cooling, and a 15 rpm agitator. The extractor is connected to a heat exchanger to prevent solvent losses during extraction. The bottom portion of extractor is connected to a gorator pump, and alternately, through a diaphragm pump to a decanter. The bottom of decanter is connected to a second extractor and a solvent stripper through a valve. The second extractor is connected through a diaphragm pump to a decanter. After a 4 hr extraction period through the gorator pump in the first extractor at 40° C., the temperature is brought down to ambient and passed through a decanter via the diaphragm pump. Ambient is considered to be between about 25° C. to about 30° C. The solid phase from the decanter is conveyed into the second extractor containing methanol (4500 L). After the second extraction period of 4 hr (at ambient temperature) the mass is passed through the diaphragm pump into the decanter. The solid phase is passed through a stripper and adhering solvent is recovered. The dry cake is stored.

The two extracts are pooled, filtered and successively passed through a falling film and wiped film evaporators operated under reduced pressure through metering pumps. The extract is thus concentrated to 95% level (450 kg) and is very viscous. The viscous mass is transferred into a 2000 L jacketed stainless steel reactor with an anchor agitator containing ethylene dichloride (1150 L) and water (50 L) under agitation. Agitation is continued for 30 minutes and stopped. The mass is then left for 1 hr for phase separation. The lower organic phase is separated, filtered and stripped under reduced pressure. The top layer containing sugars and starches is sent for aerobic treatment. The concentrate after stripping containing Neem seed constituents (350 kg) is transferred into a 3500 L stainless steel reactor containing hexane (2800 L) under agitation. The mass is stirred for 30 minutes and agitation discontinued. 15 minutes later, the hexane is transferred by suction into a 5000 L distillation still where the hexane is recovered. The residue after stripping hexane at atmospheric pressure is subjected to vacuum of 600 mm Hg to remove volatiles, and cooled to ambient temperature. The mass (80 kg) containing lipids and Neem limonoids is transferred into 500 L stainless steel reactor containing heptane (160 L) and stirred 15 minutes. It is then passed through a centrifuge where the solid limonoids are separated. The solid is then washed on the centrifuge with heptane (20 L) and spun for 15 minutes. The solid (15 kg) is then transferred into a 100 L stainless steel reactor containing methanol (45 L), agitated for 15 minutes and re-centrifuged. The solid is washed on the centrifuge with methanol (10 L) spun for 15 minutes, taken out and dried at 70° C. for 4 hr under reduced pressure (600 mm Hg). The product after drying (8 kg) is transferred into a 200 L stainless steel reactor containing methanol (160 L) under agitation. Activated carbon (1 kg) is added and heated to 90° C. under reflux. It is then passed through a pre heated 60° C. Celag leaf filter with a filter aid coating and the hot methanolic solution is passed through it and collected in another 200 L reactor. The product is allowed to crystallize without agitation and cooling. After 12 hr, the agitator is started and the product centrifuged and washed with methanol (10 L). The wet product 5 kg with 10% solvent is re-crystallized with methanol (100 L) without activated carbon. After attaining ambient temperature it is filtered and dried to yield pure Nimbin (4.0 kg).

It will be understood that various modifications may be made to the embodiments as disclosed herein. Therefore, the above description should not be construed as limiting, but merely as an exemplification of the preferred embodiments. Those skilled in the art will envision other modifications within the scope and spirit of the claims appended hereto.

All patents and references cited herein are explicitly incorporated by reference in their entirety.

REFERENCES

1. Siddiqui, *Current Science* (*India*) 11, (1942) 278.
2. Siddiqui & Mifra, *Journal of Scientific and Industrial Research* (*India*), 4 (1945) 5.
3. Narayanan et al., *Chemistry and Industry* (1962) 1283.
4. Narayanan et al., *Chemistry and Industry* (1964) 322.
5. Narayanan et al., *Chemistry and Industry* (1964) 324.
6. Harris et al., *Tetrahedron* 24 (1968) 1517.
7. *Merck Index,* 12th edition (1996) 6393.

What is claimed is:

1. A method of purifying Nimbin comprising:

a) extracting neem kernel powder with an alcoholic solvent;

b) concentrating and partitioning said extract, wherein said partitioning comprises contacting said extract with a chlorinated hydrocarbon;

c) filtering said extract of step (b);

d) contacting said extract of step (c) with an aliphatic hydrocarbon solvent;

e) clarifying said extract of step (d);

f) washing said clarified extract of step (e); and g) crystallizing the product of step (f).

2. The method of claim 1, wherein said neem kernel powder has a particle size range of about 0.1 mm to about 1.0 mm.

3. The method of claim 1, where said alcoholic solvent is added to said powder at a ratio of between about 1:1.5 to about 1:1.25 w/v.

4. The method of claim 3, wherein a said alcoholic solvent is selected from the group consisting of methanol, ethanol and isopropanol.

5. The method of claim 4, wherein said alcoholic solvent is methanol.

6. The method of claim 1, wherein said extracting in step (a) comprises two steps:

i) extracting said powder at between about 40° C. and about 50° C. for about 4 hours and ii) extracting said powder at ambient temperature for 4 hours.

7. The method of claim 1, wherein said step (b) further comprises a pooling and stripping of said extracts at a temperature not exceeding about 50° C. under a residual pressure of about 600 mm Hg.

8. The method of claim 1, wherein partitioning of step (b) comprises contacting said extracts with a chlorinated hydrocarbon selected from the group consisting of methylene dichloride, ethylenedichioride and trichioroethylene.

9. The method of claim 8, wherein said chlorinated hydrocarbon is ethylene dichloride.

10. The method of claim 8, where the chlorinated hydrocarbon layer is filtered.

11. The method of claim 10, wherein said filtered chlorinated hydrocarbon layer is stripped under a residual pressure of 600 mm Hg to form a residual mass.

12. The method of claim 11, wherein the residual mass is contacted with a hydrocarbon solvent.

13. The method of claim 12, wherein said hydrocarbon solvent is selected from the group consisting of hexane, heptane, and octane.

14. The method of claim 13, wherein said hydrocarbon is hexane.

15. The method of claim 12, wherein said mass is extracted in hydrocarbon solvent comprising the steps of:

i) stripping at atmospheric pressure and ii) stripping at a residual pressure of 600 mm Hg.

16. The method of claim 15, wherein said stripped mass is suspended and agitated in a hydrocarbon solvent.

17. The method of claim 16, wherein said hydrocarbon solvent is selected from the group consisting of hexane, heptane and octane.

18. The method of claim 1, wherein clearing and washing steps comprise:

i) centrifuging a hydrocarbon solvent containing suspension and ii) washing the resulting solid in a hydrocarbon solvent.

19. The method of claim 18, wherein said clearing and washing steps further comprise:

iii) resuspending said hydrocarbon washed solid in methanol;

iv) agitating said resuspended solid of step (iii);

v) centrifuging said resuspended solid of step (iv);

vi) washing resulting solid of step (v) in methanol; and vii) drying resulting washed solid.

20. The method of claim 19, wherein the resulting washed solid is crystallized comprising the steps of:

viii) suspending said dried solid in methanol;

ix) contacting said suspension of step (viii) with activated carbon;

x) heating said contacted suspension of step (ix) to about 90° C.; and xi) filtering said heated suspension of step (x).

21. The method of claim 20, further comprising the steps of:

xii) cooling said filtered product of step (xi);

xiii) agitating said cooled product of step (xii), wherein said product is centrifuged and subsequently washed with methanol;

xiv) recrystallizing the product of step (xiii) with methanol; and xv) filtering said product of step (xiv) with subsequent drying.

22. The method of claim 18, wherein the physicochemical properties of said isolated Nimbin include a melting point of about 210° C. to about 212° C., is essentially 98.5% pure and is tasteless.

* * * * *